United States Patent [19]
Ostermeier et al.

[11] Patent Number: 5,951,217
[45] Date of Patent: Sep. 14, 1999

[54] OPERATING DEVICE FOR A HOLLOW DRILL

[75] Inventors: Peter Ostermeier, Diessen; Rudolf Reitberger, Munich, both of Germany

[73] Assignee: Hilti Aktiengesellschaft, Schaan, Liechtenstein

[21] Appl. No.: 09/152,812

[22] Filed: Sep. 14, 1998

[30] Foreign Application Priority Data

Sep. 15, 1997 [DE] Germany .......................... 197 40 464

[51] Int. Cl.⁶ .................................................. B23B 45/00
[52] U.S. Cl. .......................... 408/59; 408/124; 408/204
[58] Field of Search .................................. 408/4, 59, 67, 408/124, 204, 710; 175/254

[56] References Cited

U.S. PATENT DOCUMENTS

| | | | |
|---|---|---|---|
| 2,349,156 | 5/1944 | Fischer | 408/124 |
| 3,452,226 | 6/1969 | Hettich | 408/124 |
| 3,546,976 | 12/1970 | Clapp et al. | 408/59 |

*Primary Examiner*—Daniel W. Howell
*Attorney, Agent, or Firm*—Brown & Wood, LLP

[57] ABSTRACT

An operating device for a hollow drill (1) including a housing (2), a drill receiving chuck (3) supported in the housing (2) for rotation relative thereto, a drive unit (4) for rotating the chuck (3), a bottom element adjoining the chuck (3) at a side of the chuck facing in a direction opposite to a drilling direction, and an arrangement for lifting the bottom element off the chuck (3).

11 Claims, 2 Drawing Sheets

OPERATING DEVICE FOR A HOLLOW DRILL

BACKGROUND OF THE INVENTION

1. Field of the Invention

The present invention relates to an operating device for a hollow drill and including a housing, a drill receiving chuck supported in the housing for rotation relative to the housing, a drive unit for rotating the drill, and a bottom element adjoining the chuck at side of the chuck facing in a direction opposite to the drilling direction.

2. Description of the Prior Art

German Utility Model No. 1,898,626 discloses a drill receiving chuck in which a hollow drill is form-lockingly secured. The chuck has a blind bore with a projection radially extending from an inner wall of the blind bore. The bottom of the blind bore forms the bottom element. The hollow drill has, in its outer surface a groove inclined partially to the longitudinal axis of the hollow drill.

For connecting the hollow drill with the drill chuck, they are fitted together and rotated in opposite direction until a free end of the hollow drill, which faces in a direction opposite to the drilling direction abuts the bottom of the blind bore which faces in the drilling direction. The hollow drill is used for forming bores in hardened structural components for anchors and for forming passages for tubular conduits. During formation of such bores and passages, drilling cores are formed in the hollow drill which should be from time-to-time from the hollow drill. The hollow drill is provided in its end facing in the drilling direction with cutting means which projects radially inward of both sides of the support body of the hollow drill. Because the outer diameter of a drilling core substantially corresponds to the inner diameter of the bore formed by the cutting means but is smaller than the inner diameter of the tubular support body of the hollow drill, the removal of the drilling core from the hollow drill from the end of the support body of the drill, which lies opposite to the cutting means, can be easily done.

In order to be able to remove the drilling core from the hollow drill in an above-described manner, it is necessary to separate the hollow drill and the chuck. This process is very time - consuming. In addition, use of special tools is required for gripping the support body in order to be able to rotate it relative to the chuck. Moreover, after an extensive drilling, the hollow drill becomes so hot that extraction of the released drill from the chuck with bare hands is not possible.

Accordingly, an object of the invention is to provide an operating device for a hollow drill which would insure quick, reliable and easy removal of a drilling core from the hollow drill in the direction opposite to the drilling direction, without the necessity to extract the hollow drill from the chuck which is secured in the operating device.

SUMMARY OF THE INVENTION

This and other objects of the present invention, which will become apparent hereinafter, are achieved by providing an operating device of the type described above and in which the bottom element can be lifted off the chuck. The lifting of the bottom element off the chuck permits to remove a drilling core, which is formed during drilling of a bore, through the chuck in the direction opposite to the drilling direction, without the need to remove the hollow drill from the chuck which, e.g., partially extends into the operating device. The bottom element can be formed, e.g., by a part of the housing of the operating device.

When a hollow drill is secured in a chuck by a threaded connection, with the hollow drill being displaced in a direction opposite to the drilling direction, a bottom element is required, against which the chuck can be displaced to insure engagement of the thread flanks. In order to prevent friction between the bottom element and an end surface of the drill which faces in a direction opposite to the drilling direction, during rotation of the drill, preferably, the bottom element is formed as a stop surface of the chuck extending perpendicular to the main axis of the chuck and which is capable of being lifted off of the stationary chuck. The stop surface is displaced away from the chuck, e.g., along the chuck main axis, a distance greater than a length of the to-be-removed drilling core.

An unhindered removal of the drilling core from the chuck in a direction opposite to the drilling direction can be insured with a stop surface which is lifted off of an axial projection of the inner dimension of the hollow drill. The stop surface can be lifted off, in this case, sidewise of the chuck.

A quick insertion and/or removal of a hollow drill which, if necessary, is provided with a shank extending into the chuck, can be achieved by inserting the drill into the chuck from a side of the chuck facing in the direction opposite to the drilling direction, and pushing the drill into the drilling direction until the drill or its shank abuts a stop edge of the chuck facing in the direction opposite to the drilling direction. The hollow drill is secured in the chuck, preferably, by a rotatable or pivotable stop surface which can be lifted off of the entire axial projection of the entire drill.

The pivotable or rotatable stop surface can be formed as a part of a handle which is formed as a separate constructional part and is connected with the housing by a fastening device. The displacement of the stop surface can advantageously be effected by the stop surface being pivoted about the fastening device which defines a pivotal axis extending substantially parallel to the chuck main axis. The fastening device may include, e.g., a rotatable eccentric with which the handle is secured to or is released from the housing so that pivoting of the stop surface and of the handle becomes possible.

According to a further development of the invention, the handle, which is formed as a separate component, can be connected with the housing by a hinge the axis of which extends, preferably, in a plane extending perpendicular to the main axis of the chuck.

Thus, lifting-off of the stop surface is effected by pivoting the stop surface about the hinge axis in a plane extending substantially parallel to the chuck main axis.

During drilling of hard structural components, very high temperatures are developed in the region of the cutting means of the drill. The wear of the cutting means is prevented with cooling medium fed to the drill during the drilling process. To provide for feeding of the cooling medium to the drill, there is provided a cooling medium channel extending through the stop surface and connected with a cooling medium source. The cooling medium channel has an outlet opening located in a plane formed by the stop surface.

As a cooling medium source, a pump arrangement, from which the cooling medium is fed into the cooling medium channel via a connecting conduit, can be used. A cooling medium cut-off device is usually provided in the housing or in the handle for cutting off the flow of the cooling medium and which is actuated when the stop surface is lifted off of the chuck. As a cut-off device, a magnetic valve can be used which is inserted into the cooling medium conduit and controls the flow of the cooling medium through the cooling medium channel to the drill.

For removing the drilling core from inside of the hollow drill, it is advantageous when the stop surface is lifted off a stationary part of the chuck, and the operating device is placed on its head to enable extraction of the drilling core. In order to prevent any damage of adjacent components of the operating device or other objects by the drill cutters when the operating device is placed on its head, a power cut-off device is actuated, upon the stop surface being lifted off, to interrupt rotation of the chuck. As a cut-off device, an electrical switch, which is connected with the connection conductor, is used. The electrical switch opens the power supply circuit as soon as the stop surface is lifted off the stationary part of the chuck.

BRIEF DESCRIPTION OF THE DRAWINGS

The features and objects of the present invention will become more apparent, and the invention itself will be best understood from the following detailed description of the preferred embodiments when read with reference to the accompanying drawings, wherein.

DETAILED DESCRIPTION OF PREFERRED EMBODIMENTS

Figure 1:
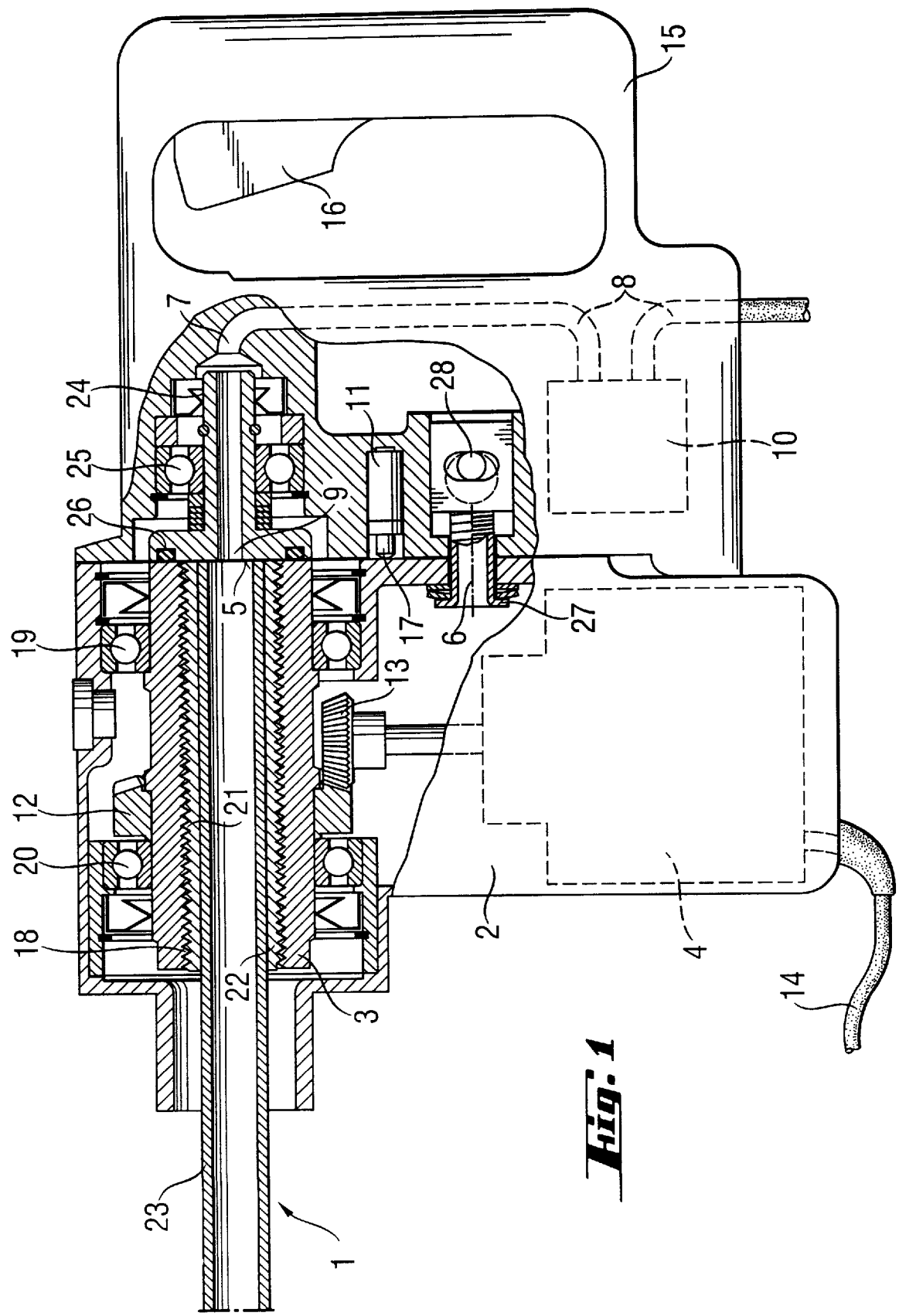
FIG. 1 shows a partially cross-sectional side view of an operating device for a hollow drill according to the present invention, with a stop surface pivotable about an axis extending parallel to the main axis of the drill chuck.
Figure 2:
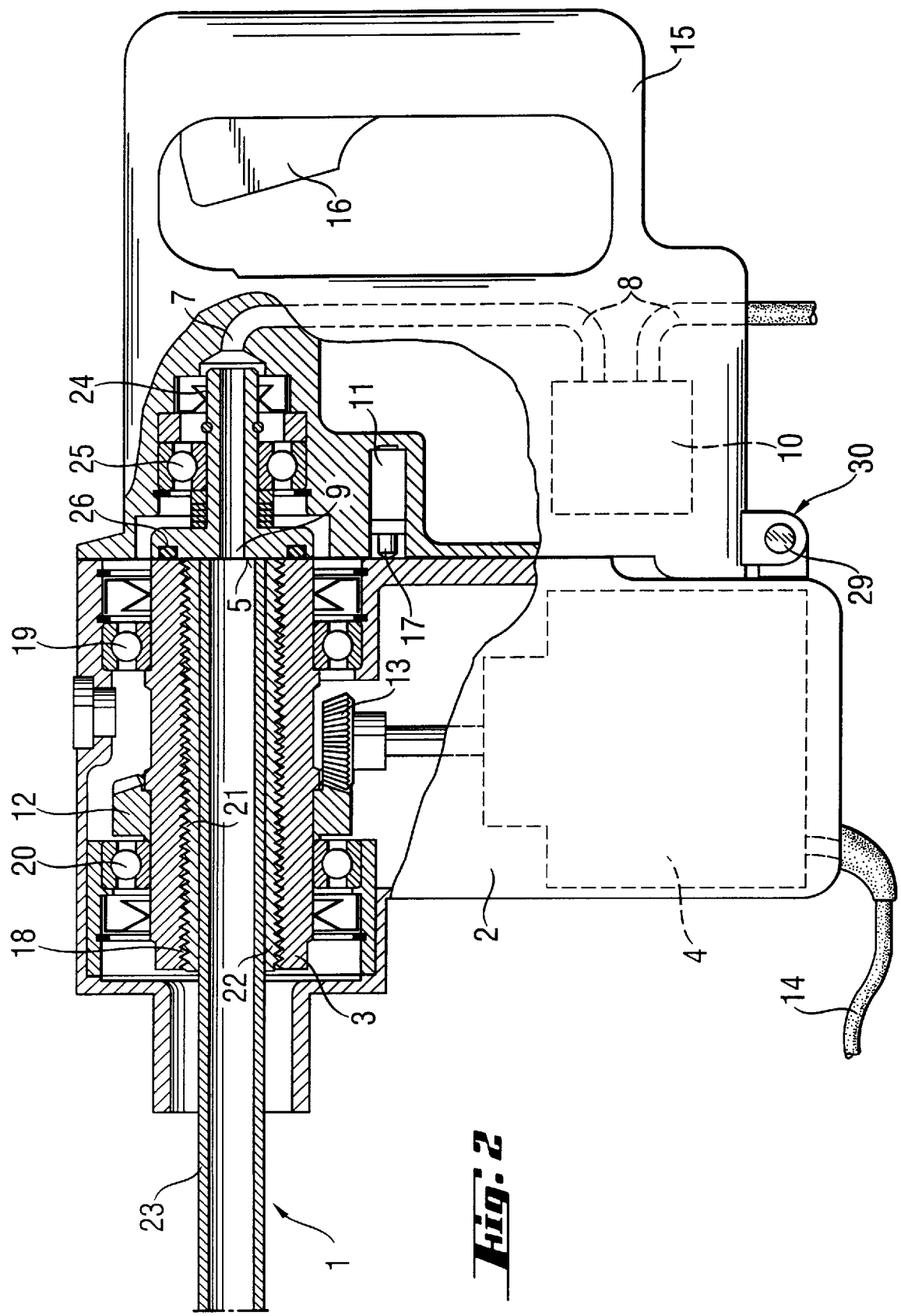
FIG. 2 shows a partially cross-sectional side view of another embodiment of an operating device for a hollow drill according to the present invention, with a stop surface pivotable in a plane extending substantially parallel to the main axis of the drill chuck.

In FIGS. 1 and 2, which show two embodiments of an operating device for a hollow drill according to the present invention and which differ from each other only by the pivotal movement of the stop surface, for sake of simplicity, the same reference numerals are used for the same elements. The only difference between the two embodiment consists, as mentioned above, in the pivotal mode of the stop surface. In FIG. 1, an axis 6 defines the pivotal mode of the stop surface, and in FIG. 2, the pivotal movement of the stop surface is defined by the hinge 30.

The operating device, which is shown in FIGS. 1–2, includes a housing 2, a handle 15 with an actuating trigger 16, a chuck 3 pivotally supported in the housing 2, and a hollow drill 1 received in the chuck 3.

Inside the housing 3, there is arranged an electrical drive unit 4 which rotates the chuck 3. The drive unit 4 is connectable with an external power source by a connection conductor 14. The drive unit 4 transmits a rotational movement to the chuck 3 via a drive shaft at the free end of there is provided a helical pinion 13 which form-lockingly cooperates with a helical gear wheel 12 fixedly connected with the chuck 3.

The longitudinal axis of the chuck 3 extends perpendicular to the longitudinal axis of the drive unit 4. The chuck 3 is supported for rotation in the housing 2 by two, spaced from each other, bearings 19 and 20. The chuck 3 has a central through-bore in which the hollow drill 1 is fixedly received. The inner wall of the chuck through-bore has an inner thread 21 which form-lockingly cooperates with an outer thread 18 of the hollow drill shank 22. The shank 22 forms a part of the hollow drill 1 and is fixedly connected with a tubular support body 23 of the hollow drill 1.

A stop surface 5, which is rotatably supported on the handle 15 and extends perpendicular to the longitudinal axis of the chuck 3 serves as an axial stop during screwing-in of the hollow drill 1 into the chuck 3 in a direction opposite to the drilling direction. A cylindrical guide region 24 adjoins the stop surface 5 at the side of the stop surface 5 opposite to the drilling direction. The guide region 24 extends through a bearing 25 which is arranged in a blind bore for the handle 15.

In the plane formed by the stop surface 5, there is located an outlet opening 9 of a channel 7, which extends through the guide region 24 and a portion of the handle 15 and which is connected by a cooling medium conduit 8 with a cooling medium supply source (not shown). A cut-off device 10, formed as a magnetic valve, interrupts the conduit 8. The cut-off device 10 interrupts flow of the cooling medium when the stop surface 5 moves away from the chuck 3.

The stop surface 5 has a circumferential groove formed in its end surface facing in the drilling direction and in which a sealing element 26 formed as an O-ring is received. The sealing element 26 is pressed against the adjacent end surface of the chuck 3 and prevent the cooling medium, which flows through the channel 7 from reaching the chuck supporting bearings 19, 20. The magnetic valve, which form the cut-off device 10, is operative connected, e.g., with actuation trigger 16. The magnetic valve blocks the flow of cooling medium through the cooling medium conduit 8.

A turn-off device 11, which is formed as an electrical switch, is mounted in the handle 15. The turn-off device 11 cuts off current flow through the connection conductor 14 and, thereby, the power supply to the drive unit 4 when the stop surface 5 moves away from the chuck 3.

The movement of the stop surface 5 away from the chuck 3 takes place in the embodiment of the operating device shown in FIG. 1 by pivotal movement of the stop surface 5 about an axis 6, which extends parallel to the main axis of the chuck 3, of a fastening device with which the handle 15 is fixedly secured to the housing 2. The axis 6 is defined by a straining screw 27 which is arranged between the handle 15 and the housing 2 and which is tightened by an eccentric 28. The eccentric 28 is connected with a clamping lever (not shown).

In a release position of the fastening device, the handle 15 is lifted off the housing 2 and is spaced from the housing 2 a short distance in a direction opposite to the drilling direction, so that the stop surface 5 and the sealing element 26 become spaced from the chuck 3. In the spaced or pivotal position of the handle 15, the spring-biased contact pin 17 of the electrical switch 11, which is mounted in the handle 15, is not any more preloaded and opens an electrical circuit responsible for feeding power to the drive unit 4, interrupting current flow to the drive unit 4.

In the embodiment of the operating device according to the present invention which is shown in FIG. 2, the stop surface 5 pivots in a plane extending parallel to the main axis of the chuck 3. To this end, the operating device includes a hinge 30 having an axle 29 which extends parallel to the plane of the stop surface 5. The stop surface 5 can be lifted off an axial projection of the inner diameter of the drill or off an axial projection of the entire drill.

Though the present invention was shown and described with references to the preferred embodiments, various modifications thereof will be apparent to those skilled in the art and, therefore, it is not intended that the invention be limited to the disclosed embodiments or details thereof, and departure can be made therefrom within the spirit and scope of the appended claims.

What is claimed is:

1. An operating device for a hollow drill (1), comprising a housing (2); a drill receiving chuck (3) supported in the housing (2) for rotation relative thereto; a drive unit (4) for rotating the chuck (3); bottom means adjoining the chuck (3) at a side of the chuck facing in a direction opposite to a drilling direction; and means for lifting the bottom means off the chuck (3).

2. An operating device according to claim 1, wherein the bottom means is formed by a stop surface (5) which limits displacement of the chuck in the direction opposite to the drilling direction and which extends perpendicular to main axis of the chuck (3).

3. An operating device according to claim 2, wherein the stop surface (5) is lifted off an axial projection of an inner dimension of the hollow drill.

4. An operating device according to claim 2, wherein the stop surface (5) is lifted off an axial projection of the entire hollow drill (1).

5. An operating device according to claim 3, wherein lifting-off of the stop surface (5) is effected by a pivotal movement of the stop surface (5) about an axis extending substantially parallel to the main axis of the chuck (3).

6. An operating device according to claim 3, wherein lifting-off of the stop surface (5) is effected by a pivotal movement of the stop surface (5) in a plane extending substantially parallel to the main axis of the chuck (3).

7. An operation device according to claim 4, wherein lifting-off of the stop surface (5) is effected by a pivotal movement of the stop surface (5) about an axis extending substantially parallel to the main axis of the chuck (3).

8. An operating device according to claim 4, wherein lifting-off of the stop surface (5) is effected by a pivotal movement of the stop surface (5) in a plane extending substantially parallel to the main axis of the chuck (3).

9. An operating device according to claim 2, further comprising a cooling medium channel (7) extending through the stop surface (5) and connected with a cooling medium source, the cooling medium channel (7) having an outlet opening located in a plane formed by the stop surface (5).

10. An operating device according to claim 9, further comprising means (10) for interrupting supply of cooling medium, the interrupting means (10) being actuated in response to the lifting-off of the stop surface (5).

11. An operating device according to claim 2, further comprising means (11) for interrupting a rotational movement of the chuck (3) in response to the lifting-off of the stop surface (5).

* * * * *